(12) United States Patent
Itagaki (10) Patent No.: US 7,118,219 B2
(45) Date of Patent: Oct. 10, 2006

(54) TEST TOOL FOR OPTOMETRY

(75) Inventor: Takashi Itagaki, Tokyo (JP)

(73) Assignee: Hoya Corporation, Tokyo (JP)

( * ) Notice: Subject to any disclaimer, the term of this patent is extended or adjusted under 35 U.S.C. 154(b) by 380 days.

(21) Appl. No.: 10/388,800

(22) Filed: Mar. 14, 2003

(65) Prior Publication Data

US 2003/0174282 A1 Sep. 18, 2003

(30) Foreign Application Priority Data

Mar. 18, 2002 (JP) ............................. 2002-074804

(51) Int. Cl.
*A61B 3/10* (2006.01)

(52) U.S. Cl. .................................... 351/216
(58) Field of Classification Search ................ 351/216, 351/205, 200
See application file for complete search history.

(56) References Cited

U.S. PATENT DOCUMENTS

| 1,002,580 | A | * | 9/1911 | Griffin ........................ 351/228 |
| 1,258,417 | A | | 3/1918 | Kellner |
| 2,147,448 | A | | 2/1939 | Lee |
| 2,147,488 | A | | 2/1939 | Hickman et al. |
| 4,220,402 | A | | 9/1980 | Jannelli |
| 4,236,793 | A | | 12/1980 | Whitney et al. |
| 5,499,063 | A | * | 3/1996 | Butler et al. .................. 351/54 |
| 5,880,805 | A | | 3/1999 | Naessens et al. |
| 6,132,045 | A | * | 10/2000 | Gauvreau ................... 351/204 |
| 6,270,219 | B1 | * | 8/2001 | Saito .......................... 351/169 |
| 6,325,506 | B1 | * | 12/2001 | Cooper ....................... 351/47 |

FOREIGN PATENT DOCUMENTS

JP 05-46725 U 12/1993

* cited by examiner

*Primary Examiner*—Eric F. Winakur
*Assistant Examiner*—Theodore Shih
(74) *Attorney, Agent, or Firm*—Brown Raysman Millstein Felder & Steiner LLP (57) ABSTRACT

An test tool for optometry includes a lens holding frame and a clip. The lens holding frame pivotally supports a trial lens to be mounted. The clip is attached to a rear side of the lens holding frame to clamp glasses. The lens holding frame has a pair of axi-symmetrical C-shaped rims having open ends and opposing closed ends, and a connecting portion that connects the opposing closed ends of the rims. Each rim has an inner surface that forms an accommodating space for holding the trial lens to be pivotal and movable in a left-to-right direction.

11 Claims, 6 Drawing Sheets

TEST TOOL FOR OPTOMETRY

BACKGROUND OF THE INVENTION

The present invention relates to a test tool for optometry and, more particularly, to a test tool for optometry suitably used for mounting a progressive multifocal trial lens.

Along with aging in the recent protracted-life society, demands for presbyopic lenses have increased. In particular, progressive multifocal lenses have become popular very widely, and their types have become vary. In order to let the wearers know the design characteristics of the progressive multifocal lenses, it is preferable to have the wearer actually wear lenses that may be appropriate, and to test the individual lenses. It is, however, not easy to create an atmosphere for trying a trial lens accurately. More specifically, the eye points are adjusted using an optometrical frame for testing. Then, the state of the glasses, other than presbyopic lenses, that the wearer currently wears is created by combining general trial lenses, and trial for the progressive multifocal trial lenses is started. Therefore, various types of adjusting operations such as mounting trial lenses, adjustment of lens combinations, adjusting operation of the pupillary distance (to be referred to as PD hereinafter), adjustment of the cylinder axis, and adjustment of the eye points are inevitable. Hence, preparation for wearing takes time, and the setting operation for the wearing state is not easy.

A person with astigmatism or a high-dioputric power shortsighted person needs a large number of lenses to be combined, and progressive multifocal lenses are added to these lenses. Hence, the thicknesses and weights of the lens portions increase, imposing a burden to the wearer.

Conventionally, various types of optometrical frames have been proposed to be used for testing the vision of a person to be tested (for example, see Japanese Utility Model Publication No. 5-46725 (claims, line 39, lower left column of page 2 to line 15, right column of page 9, and FIGS. 1 and 3).

Note that the present applicant did not reach a preceding technical reference closely related to the present invention other than that specified by the information in the preceding technical reference described in this specification.

The optometrical frame described in Japanese Utility Model Publication No. 5-46725 comprises a front mounting integrally having a pair of left and right temples for clamping the side head portions of the wearer, a pair of left and right lens holders attached to the front surface of the front mounting to be movable in the right-to-left direction, a lens holder holding member for holding the lens holders together with the front mounting, and a nose pad detachably attached to the front mounting. Usually, the optometrical frame is mounted on the person to be tested by placing the nose pad against the person's nose, and the wearer's eyesight is examined. When the wearer's eyesight is to be examined with his glasses on, a hanger is attached to the front mounting in place of the nose pad, and is placed on the upper surfaces of the rims of the glasses, so that the optometrical frame is stabilized. Then, the wearer's eyesight is tested with the trial lenses mounted on the lens holders and the lenses of the glasses being placed one upon another.

As the optometrical frame described in Japanese Utility Model Publication No. 5-46725 has the front mounting, two lens holders, lens holder holding member, nose pad, hanger, and the like, the number of components is accordingly large, the weight of the optometrical frame cannot be decreased, and the manufacturing cost is high. When the wearer's eyesight is to be tested with his glasses on, the nose pad must be exchanged for the hanger, which is cumbersome. When the optometrical frame is to be used as it is mounted on the glasses, its entire weight acts on the nose through the glasses, imposing a great burden to the nose. Also, the temples (a total of 4) of the glasses and optometrical frame are placed on the ears and side head portions. Thus, if the optometry takes time, the wearer feels the four temples annoying.

The present invention has been made to solve the conventional problems described above, and has as its object to provide a test tool for optometry which is simple and has a small number of components to enable weight reduction and cost reduction, and which can be worn to be overlaid on the existing glasses.

SUMMARY OF THE INVENTION

It is, therefore, the principal object of the present invention to provide a test tool for optometry which can be worn to be overlaid on the existing glasses and requires a smaller number of components than in the prior art, and the weight of which is accordingly decreased, enabling cost reduction.

It is another object of the present invention to provide a test tool for optometry with which eyesight can be tested within a shorter test time than in the prior art.

It is still another object of the present invention to provide a test tool for optometry with which trial lenses to be mounted can be positioned easily without requiring any special operation.

In order to achieve the above objects, according to the present invention, there is provided a test tool for optometry comprising a lens holding frame for pivotally supporting a trial lens to be mounted, and a clip attached to a rear side of the lens holding frame to clamp glasses, wherein the lens holding frame comprises a pair of axi-symmetrical C-shaped rims having open ends and opposing closed ends, and a connecting portion that connects the opposing closed ends of the rims, and each of the rims has an inner surface that forms an accommodating space for holding the trial lens to be pivotal and movable in a left-to-right direction.

DESCRIPTION OF THE PREFERRED EMBODIMENTS

The present invention will be described in detail by way of embodiments shown in the accompanying drawings.

FIGS. 1 to 5 show a test tool for optometry according to an embodiment of the present invention. In FIGS. 1 to 5, a test tool for optometry 1 is used as it is mounted on glasses 2 worn by the person to be tested, and is formed of a lens holding frame 3 and a clip 4 attached to the center of the rear surface of the lens holding frame 3. When the person to be tested does not wear the glasses 2, ready-made glasses provided to the optician's shop are used. The lens degree of the ready-made glasses is 0.00 diopter (D).

Figure 1:
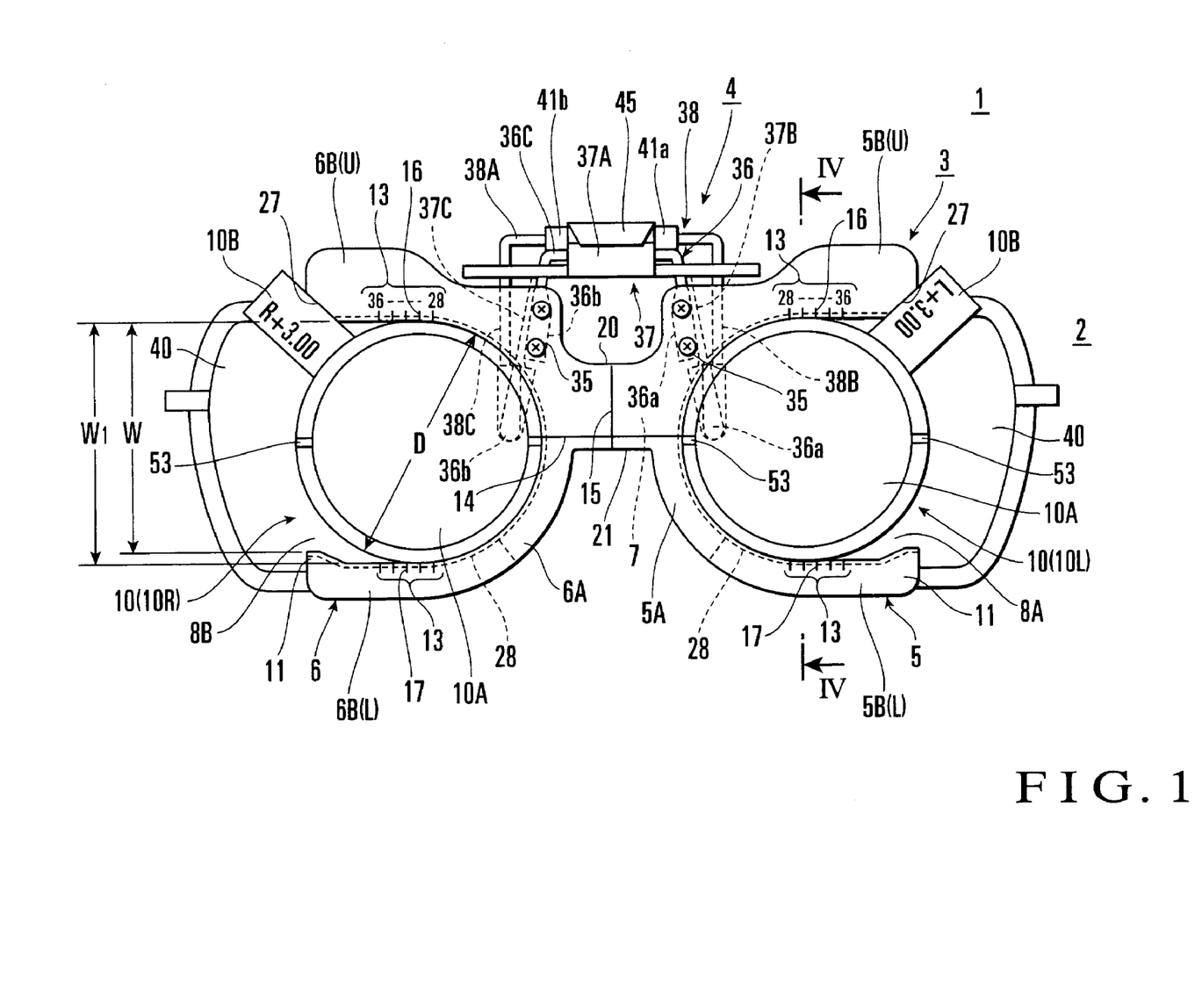
FIG. 1 is a front view of a test tool for optometry in a use state according to one embodiment of the present invention.

The lens holding frame 3 has two rims 5 and 6 and a connecting portion 7, as shown well in FIG. 1. The rims 5 and 6 have the same C shape so each of them has an open end and closed end. The closed ends oppose each other, while the open ends face sideways. The connecting portion 7 connects the closed ends of the rims 5 and 6.

Inner spaces 8A and 8B of the respective C-shaped rims 5 and 6 form accommodating spaces for accommodating trial lenses 10. The mounted trial lenses 10 are accommodated to be pivotal and movable in the left-to-right direction in the accommodating spaces 8A and 8B. Hence, the rim 5 is formed of a semicircular portion 5A, and two horizontal straight portions 5B (U) and 5B (L) continuous to the semicircular portion 5A and vertically opposing each other to be parallel to each other. The rim 6 is formed of a semicircular portion 6A, and two horizontal straight portions 6B (U) and 6B (L) continuous to the semicircular portion 6B and vertically opposing each other to be parallel to each other. These straight portions enable the trial lenses 10 to move in the inner spaces 8A and 8B in the left-to-right direction (PD adjustment and eye point adjustment). For example, the diameters of the semicircular portions 5A and 6A of the respective rims 5 and 6, a width $W_1$ of the two vertically opposing straight portions 5B (U) and 5B (L), and that of the two vertically opposing straight portions 6B (U) and 6B (L) are 36 mm and are accordingly equal, and are set smaller than the outer diameter (38 mm) of the trial lenses 10. A vertical width (width of the open end) W of the open end of each of the rims 5 and 6 is set smaller than the width $W_1$ ($W_1$>W) due to the presence of a projection 11, so that the trial lenses 10 are prevented from dropping.

PD-adjustment distance scales 13 are formed on the outer surfaces (the straight portions described above) of the rims 5 and 6, respectively. Two lines 14 and 15 are formed on the connecting portion 7 that connects the closed ends of the rims 5 and 6.

The PD-adjustment distance scale 13 is formed on each of the upper (U) and lower (L) straight portions 5B (U) and 5B (L) and, 6B (U) and 6B (L) on the outer surfaces of the rims 5 and 6, as shown in FIG. 1. In this case, each of the upper straight portions 5B (U) and 6B (U) has figures "28", "30", "32", "34", and "36" (30, 32, and 34 are not shown) respectively expressing the half-widths (mm) of the PD and indicating the distances from the center of the lens holding frame 3, and five equidistant vertical scale marks 16 indicating the positions of these distances. The surface of each of the lower straight portions 5B (L) and 6B (L) only has five vertical scale marks 17 respectively indicating distances "28", "30", "32", "34", and "36" from the center of the lens holding frame 3. The PD adjustment range of the trial lenses 10 is 56 mm to 72 mm in this embodiment.

Of the two lines 14 and 15 formed on the surface of the connecting portion 7, the horizontal line 14 is a datum line (geometric horizontal line) running through the centers of the rims 5 and 6. The vertical line 15 indicates the center in the left-to-right direction of the test tool for optometry 1. When the test tool for optometry 1 is to be mounted on the glasses 2, it is mounted such that the vertical line 15 coincides with the center of the bridge, so that a shift in the left-to-right direction is adjusted.

A rectangular recess 20 is formed above the connecting portion 7, and a nose relief recess 21 is formed under the connecting portion 7. The recess 20 serves to prevent the interference of the lens holding frame 3 and clip 4 which occurs when they pivot relative to each other, and to enable the clip 4 to operate, and is formed with a size that enables insertion of a thumb or index finger. The nose relief recess 21 prevents the nose of the person to be tested from abutting against the lens holding frame 3 when the test tool for optometry 1 is mounted on the glasses 2, and is formed to have an axi-symmetrical trapezoid (preferably like a mountain with a flat top portion whom seen from a side).

The projections 11 formed on the open ends of the rims 5 and 6 are formed of, e.g., triangular projections, and integrally stand upright on the upper surfaces of the distal ends of the lower straight portions 5B (L) and 6B (L), respectively.

When the trial lenses 10 are to be mounted in the accommodating spaces 8A and 8B of the rims 5 and 6, the vertically opposing straight portions 5B (U) and 5B (L), and 6B (U) and 6B (L) of the rims 5 and 6 may be elastically deformed against the elasticity of the lens holding frame 3 itself to separate from each other, so that the open end widths W become larger than the outer diameters D of the trial lenses 10. When the trial lenses 10 are to be removed from the accommodating spaces 8A and 8B, they may be pulled to ride over the corresponding projections 11. At this time, the vertically opposing straight portions 5B (U) and 5B (L), and 6B (U) and 6B (L) of the rims 5 and 6 elastically deform in a direction to separate from each other, and the open end widths W become larger than the outer diameters D of the trial lenses 10. Thus, the trial lenses 10 can be pulled out easily.

Tilted surfaces 27 for positioning the trial lenses 10 at the positions of PD 56 mm are formed on the lower corners of the distal ends of the upper straight portions 5B (U) and 6B (U) of the rims 5 and 6, respectively. The tilted surfaces 27 are respectively tilted at angles of 45° toward the substantial centers of the rims 5 and 6.

Lens holding grooves 28 for holding the outer peripheries of the trial lenses 10 are formed in those respective inner surfaces of the rims 5 and 6 which face the accommodating spaces 8A and 8B, throughout the entire circumferences. Each lens holding groove 28 forms a V-shaped groove, as shown in FIG. 4, with its lower groove width being larger than its upper groove width.

Figure 4:
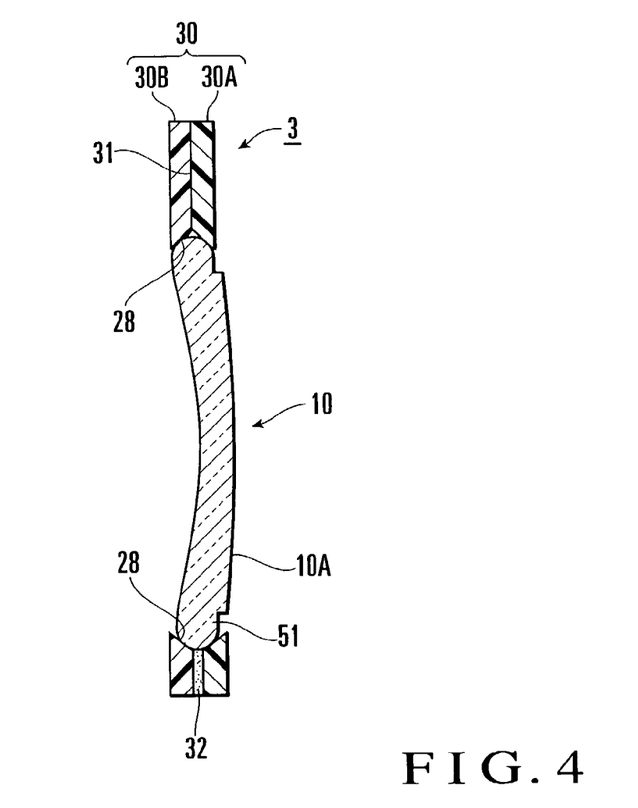
FIG. 4 is an enlarged sectional view taken along the direction of the line IV—IV in FIG. 1.

For example, this lens holding frame 3 is integrally formed by placing one upon another and bonding two transparent flat plastic plates 30 (denoted by 30A when referring to an obverse plastic plate and by 30B when referring to a reverse plastic plate) having the same shape, as is shown well in FIG. 4. The two plastic plates 30A and 30B are formed of an acrylic resin to thicknesses of about 1.5 mm, to each have the shape of two letters "C" (or letters "U" inverted sideways) that are bonded together back to back (or the shape of a figure "8" inverted sideways after removing its upper and lower portions). The upper portions of the plastic plates 30A and 30B are adhered to each other with an adhesive 31 (FIG. 4), and their lower portions are bonded to each other with a double-sided adhesive tape 32 having a thickness of about 1 mm. The distance between the lower ends of the two plastic plates 30A and 30B is set larger than that between their upper ends by the presence of the double-sided adhesive tape 32. This aims at increasing the insertion amounts of the trial lenses 10 into the lower lens holding grooves 28 to be larger than those in the upper side, so that the trial lenses 10 are prevented from dropping from the lens holding grooves 28. The inner circumferential surfaces of the rims of the respective plastic plates 30A and 30B form tilted surfaces that are tilted at the same angle but in the opposite directions, thus forming the lens holding grooves 28. Each lens holding groove 28 has a depth of about 1.5 mm.

Figure 2:
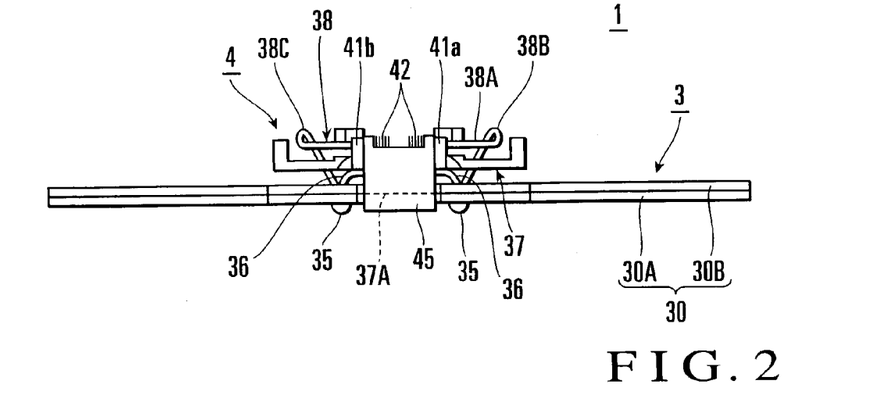
FIG. 2 is a plan view of the test tool for optometry shown in FIG. 1.
Figure 3:
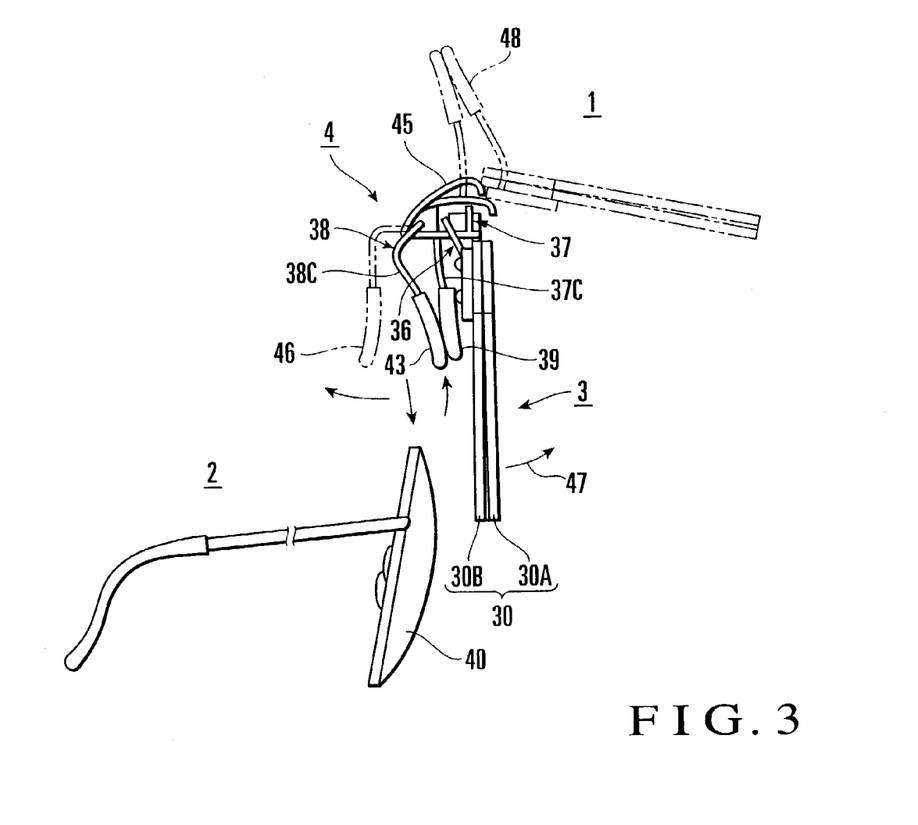
FIG. 3 is a view showing how the test tool for optometry shown in FIG. 1 is mounted on glasses.

Referring to FIGS. 1 to 3, the clip 4 is used to attach the lens holding frame 3 to the glasses 2. The clip 4 is formed of an entirely C-shaped support arm 36 fixed to the upper portion of the rear surface of the lens holding frame 3 with four machine screws 35, a pivotal member 37 attached to the central portion of the support arm 36 to be vertically pivotal, a clamp member 38 pivotally attached to the pivotal member 37, and the like.

The support arm 36 is formed of a thin metal rod. Two ends of the support arm 36 are formed flat and bent downward to form legs 36a and 36B. The legs 36a and 36b are fixed by the machine screws 35 such that they are located on the rear surface of the lens holding frame 3 and on the two sides of the recess 20. A central portion 36C of the support arm 36 is horizontal and is located above the recess 20 of the lens holding frame 3, to form a shaft for pivotally, axially supporting the pivotal member 37.

The pivotal member 37 has a gripping portion 37A located above the recess 20. A pair of left and right front clamp portions 37B and 37C integrally extend downward from the two sides of the gripping portion 37A. The lower ends of the front clamp portions 37B and 37C are covered with caps 39 made of a soft material, so they do not damage lenses 40 of the glasses 2 upon abutting against them. A pair of left and right bearings 41a and 41b for pivotally, axially supporting the clamp member 38 are integrally formed on the rear end of the upper surface of the pivotal member 37.

The clamp member 38 is formed of a thin metal rod. A central portion 38A of the clamp member 38 is horizontal and detachably fitted in the two bearings 41a and 41b of the pivotal member 37. Thus, the clamp member 38 is pivotally, axially supported. Also, the clamp member 38 is biased by two torsion coil springs 42 in one direction (counterclockwise in FIG. 3). The torsion coil springs 42 are mounted on the central portion 38A of the clamp member 38, and has one end pressed by the pivotal member 37 and the other end pressed by the clamp member 38. The two ends of the clamp member 38 are bent downward to oppose the front clamp portions 37B and 37C of the pivotal member 37, thus forming rear clamp portions 38B and 38B, respectively. The rear clamp portions 38B and 38C are covered with caps 43 made of a soft material, so they do not damage the lenses 40 of the glasses 2 upon abutting against them. As shown in FIG. 3, the rear clamp portions 38B and 38C are usually pressed from behind by the spring forces of the torsion coil springs 42 against the front clamp portions 37B and 37C of the pivotal member 37. More specifically, the front clamp portions 37B and 37C of the pivotal member 37 and the rear clamp portions 38B and 38C of the clamp member 38 form a clamping means for clamping the obverse and reverse surfaces of the lenses 40 of the glasses 2. This allows the test tool for optometry 1 to be mounted on the glasses 2. An operation lever 45 is integrally formed at the central portion 38A of the clamp member 38. The operation lever 45 forms a shape with a circular arc-like portion when seen from a side, as shown in FIG. 3, and covers the upper portion of the gripping portion 37A of the pivotal member 37.

When the obverse and reverse surfaces of the lenses 40 of the glasses 2 are to be clamped with the front clamp portion 37B and 37B and the rear clamp portions 38B and 38C, the gripping portion 37A of the pivotal member 37 and the operation lever 45 are held by the thumb and index finger, and the operation lever 45 is pivoted clockwise in FIG. 3 against the torsion coil springs 42. Hence, the clamp member 38 pivots clockwise in FIG. 3 to separate the rear clamp portions 38B and 38C away from the front clamp portions 37B and 37C, as indicated by an alternate long and two short dashed line 46 in FIG. 3. In this state, the lenses 40 of the glasses 2 are inserted between the clamping portions 38B and 38C, and 37B and 37C from below, and the pressing force on the operation lever 45 is canceled. Then, the clamp member 38 pivots backward by the forces of the torsion coil springs 42, and the front clamp portions 37B and 37C, and the rear clamp portions 38B and 38C clamp the obverse and reverse surfaces of the lenses 40. Thus, the test tool for optometry 1 is mounted on the glasses 2.

In the clip 4 with the above structure, the pivotal member 37 is attached to the central portion 36C of the support arm 36 so as to be pivotal upward within the angular range of almost 180°, thus forming a flip-up clip. More specifically, with the test tool for optometry 1 being mounted on the glasses 2, when the lens holding frame 3 is lifted forward as indicated by an arrow 47 in FIG. 3, the support arm 36 pivots with respect to the pivotal member 37, so that the lens holding frame 3 can flip up in a substantially horizontal or substantially vertical state. When the trial lenses 10 are to be mounted on the rims 5 and 6, respectively, of the lens holding frame 3, the pivotal member 37 and clamp member 38 are flipped up above the lens holding frame 3, as indicated by an alternate long and two short dashed line 48. Then, the trial lenses 10 can be reliably mounted on the lens holding frame 3 without abutting against the front clamp portions 37B and 37C.

Figure 5:
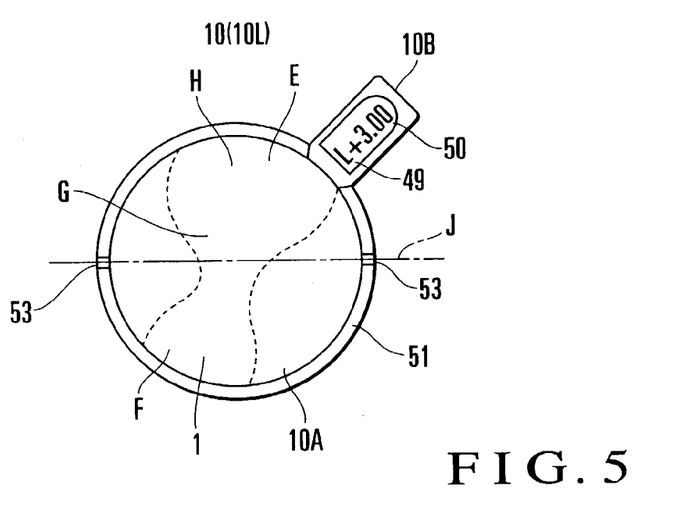
FIG. 5 is a front view of a left-eye trial lens to be used in the test tool for optometry described above.

Referring to FIGS. 4 and 5, each trial lens 10 is formed of a transparent synthetic resin injection-molded product, and is comprised of a lens portion 10A and a plate-like nip portion 10B integrally extending from part of the outer periphery of the lens portion 10A in the radial direction. The lens portion 10A has a distance portion E, a reading portion F, and a progressive portion G for connecting the two portions E and F, thus forming a progressive multifocal trial lens. Reference numeral H denotes the position of the eye point of the distance portion E; and I, the position of the eye point of the reading portion F.

The nip portion 10B is formed on either the left or right side of the position of the optical center of the lens portion 10A in accordance with whether the lens portion 10A is for the left eye (L) or the right eye (R), to be tilted at 45° with respect to the horizontal and vertical lines. More specifically, in the case of a left-eye trial lens 10L, the nip portion 10B projects upward at an angle of 45° from the position of 45° to the left of the lens portion 10A when seen by the person to be tested. In the case of a right-eye trial lens 10R, the nip portion 10B projects upward at the angle of 45° from the position of 45° to the right of the lens portion 10A when seen by the person to be tested.

The nip portion 10B has a letter (L or R) 49 for discriminating whether the trial lens 10 is for the right eye or left eye, and a figure 50 indicating the addition (D) of the lens portion 10A on its surface. The lens portion 10A integrally has a rim 51, to be held by the corresponding lens holding groove 28 of the lens holding frame 3, on its outer surface throughout the entire circumference. The rim 51 has two marks 53, indicating the direction of the horizontal reference line, on the left and right sides of the surface of the rim 51. The marks 53 are formed of small recesses in the surface of the rim 51. The trial lens 10 is mounted in the lens holding groove 28 of the lens holding frame 3 such that an imaginary line J (see FIG. 5) connecting the two marks 53 becomes horizontal, in other words, such that the nip portion 10B is directed obliquely upward at 45°. The rim 51 of the trial lens 10 is held by the lens holding groove 28, and angle adjustment is performed such that the imaginary line J connecting the two marks 53 becomes horizontal. Then, in the case of the left-eye trial lens 10L, its nip portion 10B closely opposes or abuts against the tilted surface 27 of the left rim 5, as shown in FIG. 1. In the case of the right-eye trial lens 10R, its nip portion 10B closely opposes or abuts against the tilted surface 27 of the right rim 6. In this state, the horizontal line 14 formed at the center of the front surface of the lens holding frame 3 and the imaginary line J connecting the two marks 53 form one straight line. When the lens portion 10A is inserted to the innermost deep end of the lens holding groove 28 so the nip portion 10B abuts against the tilted surface 27, the PD value (the distance from the center of the lens holding frame 3) is adjusted to 28 mm.

The test tool for optometry 1 with the above structure is comprised of the lens holding frame 3 formed by the two plastic plates 30A and 30B, and the clip 4 attached to the center of the rear surface of the lens holding frame 3. Thus, the structure is simple and the number of components is very small, so that weight reduction is enabled, and the test tool for optometry 1 can be fabricated at a low cost. The test tool for optometry 1 can be mounted on and removed from the glasses 2 simply and easily, and the trial lenses can be inserted in and removed from the lens holding grooves 28 simply and easily, thus providing a test tool for optometry that can be handled easily.

As the test tool for optometry 1 is lightweight, even when the person to be tested wears it for a long period of time, the physical burden is small, so that his eyesight can be tested while he wears it comfortably. Particularly, this test tool for optometry 1 is suitably used when the person to be tested is to experience how he can see a far portion and near portion with upper-plane-type (with the power of the distance portion being 0.00) progressive multifocal trial lenses on.

The flip-up-type clip 4 can flip up and down the lens holding frame 3 freely. Each time optometry is to be temporarily stopped, the test tool for optometry 1 need not be removed from the glasses 2, but the lens holding frame 3 need only be flipped up manually, so as to use only the glasses 2.

When the trial lenses 10 are to be mounted on the test tool for optometry 1, the clip 4 may be flipped up above the lens holding frame 3 in advance. Then, the trial lenses 10 can be mounted reliably without abutting against the caps 39 of the front clamp portions 37B and 37C of the clip 4.

PD adjustment and eye point adjustment can be performed easily by moving the trial lenses 10 to the left and right in the lens holding grooves 28, or by vertically adjusting the clamp positions of the trial lenses 10 by means of the front clamp portions 37B and 37C of the pivotal member 37 and the rear clamp portions 38B and 38C of the clamp member 38.

Figure 6:
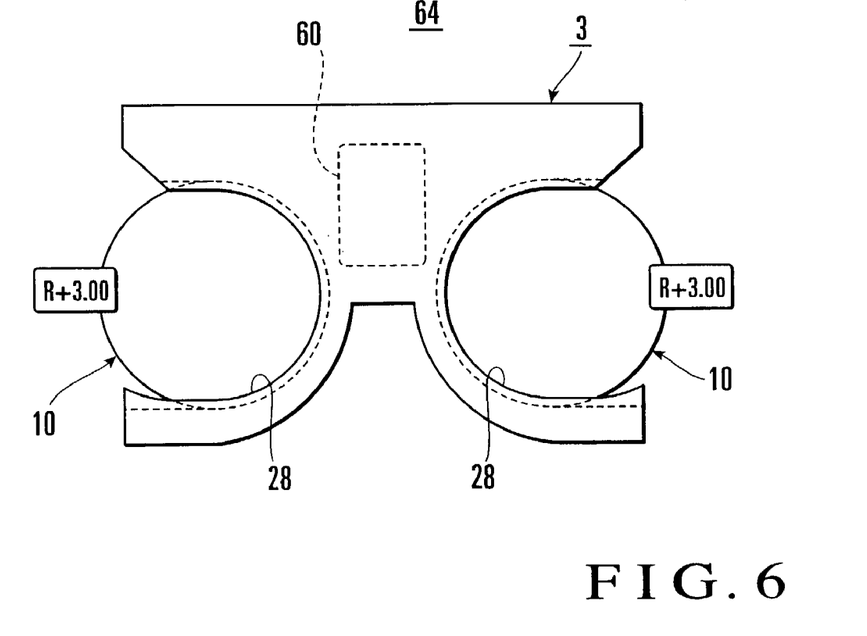
FIG. 6 is a front view of a test tool for optometry according to another embodiment of the present invention.
Figure 7:
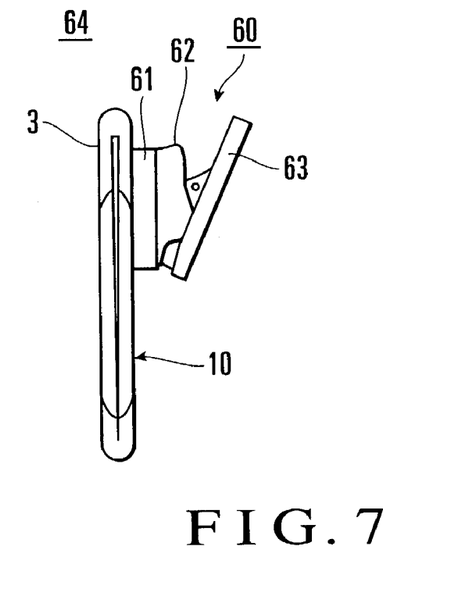
FIG. 7 is a side view of the test tool for optometry shown in FIG. 6.
Figure 8:
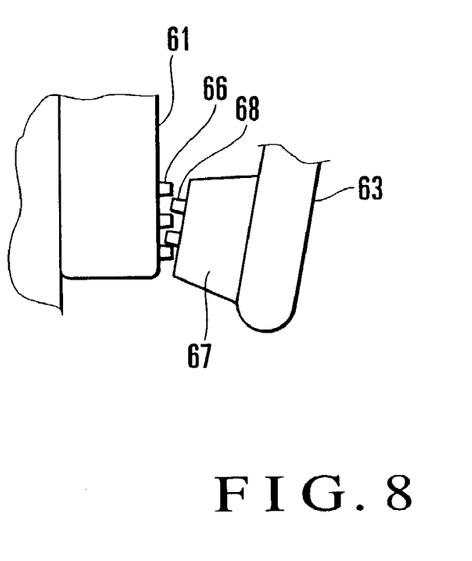
FIG. 8 is an enlarged view of the main part.

FIGS. 6 to 8 show a test tool for optometry according to another embodiment of the present invention. According to this embodiment, as best shown in FIG. 6, a lens holding frame 3 and a clip 60 attached to the center of the rear surface of the lens holding frame 3 form a test tool for optometry 64. The bridge of the glasses is clamped by the clip 60.

The lens holding frame 3 is formed of two plastic plates with the same shape, in the same manner as in the embodiment (described above) shown in FIGS. 1 to 5. In second embodiment, no adhesive is used, but two plastic plates are placed one upon another and integrally bonded to each other through a double-sided adhesive tape, so that the two plastic plates oppose each other to be parallel to each other. Also, the lens holding frame 3 has no recess 20 above its center. The second embodiment is different from the first embodiments only in these respects. Except for that, the structure of the second embodiment is substantially the same as that of the first embodiment, and a detailed thereof will accordingly be omitted.

The clip 60 is formed of a clip base 61 fixed to the center of the rear surface of the lens holding frame 3, and a movable clamp piece 63 pivotally attached to the clip base 61 through a leaf spring 62. The movable clamp piece 63 and clip base 61 clamp the bridge of the glasses. More specifically, this embodiment uses a simple clip which is not a flip-up clip.

A plurality of ridges 66 extending in the left-to-right direction project from the surface of the lower end of the clip base 61 at predetermined gaps in the direction of height, as shown in FIG. 8. A projection 67 projects integrally from the inner surface of the lower end of the movable clamp piece 63. A plurality of ridges 68 extending in the left-to-right direction project from that surface of the projection 67 which opposes the surface of the lower end of the clip base 61, at predetermined gaps in the direction of height. The ridges 66 and 68 are formed to be shifted from each other by half pitch. When the ridges 68 engage with the ridges 66, they form a horizontal holding mechanism that prevents tilt of the movable clamp piece 63 in the left-to-right direction and holds the movable clamp piece 63 horizontally.

In the test tool for optometry 64 with this structure, in the same manner as in the embodiment described above, the structure is simple, and the number of components is small. Particularly, the arrangement of the clip 60 is simplified to enable weight reduction and cost reduction. Also, the test tool for optometry 64 can be mounted on and removed from the glasses easily, and the trial lenses 10 can be inserted in and removed from the lens holding grooves 28 easily. Thus, a test tool for optometry that can be handled easily can be provided.

FIGS. 9 to 12 show still another embodiment of the present invention.

Figure 9:
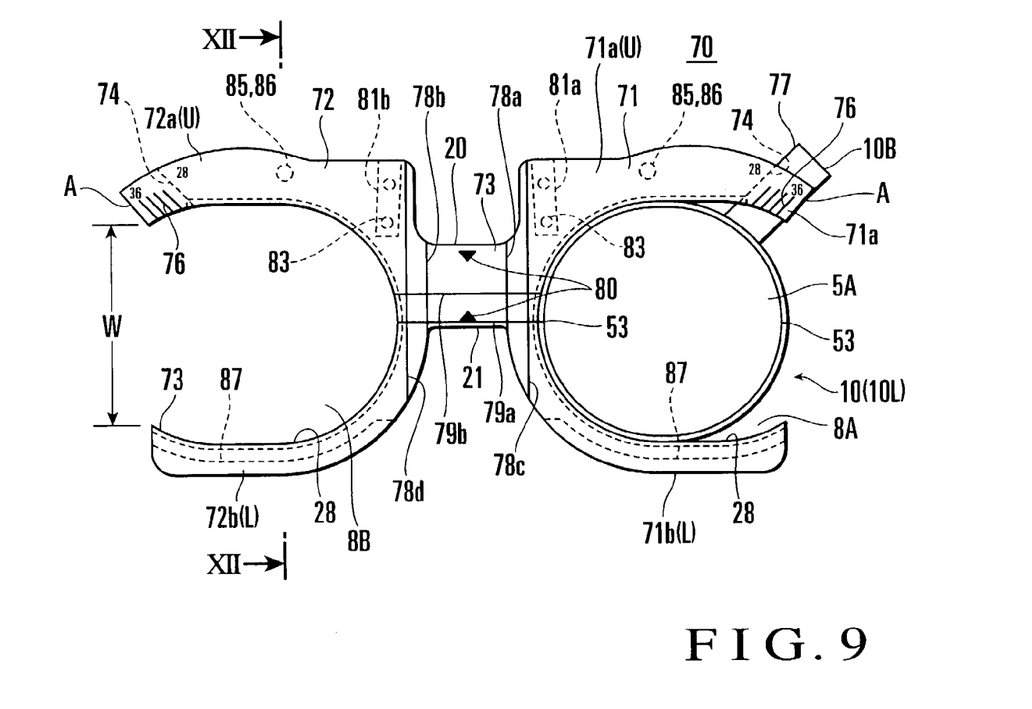
FIG. 9 is a front view of a lens holding frame showing still another embodiment of the present invention.

A lens holding frame 70 of this embodiment is formed by placing one upon another two plastic plates 30A and 30B which have substantially the same shape as that of the lens holding frame 3 of the embodiment shown in FIG. 1. Hence, the lens holding frame 70 has a pair of axi-symmetric C-shaped (or sideway-inverted U-shaped) rims 71 and 72 and a connecting portion 73. Each of the rims 71 and 72 has an open end and closed end. The closed ends oppose each other. The connecting portion 73 connects the closed ends of the rims 71 and 72.

Inner spaces 8A and 8B of the rims 71 and 72 form accommodating spaces where trial lenses 10 are to be detachably inserted. Lens holding grooves 28 for holding trial lenses 10 to be pivotal and movable in the left-to-right direction are formed in the respective inner surfaces of the rims 71 and 72. The distal ends of upper (U) and lower (L) straight portions 71a (U) and 71b (L) of the rim 71 and the distal ends of upper (U) and lower (L) straight portions 72a (U) and 72*b* (L) of the rim 72 are curved with appropriate radii of curvature so they come close to each other. Thus, an open end width W of the rims 71 and 72 is set smaller than the outer diameter of the trial lenses 10. In this case, the distal ends of the upper and lower straight portions 71*a* (U) and 71*b* (L) of the plastic plate 30A on the obverse side; and the distal ends of the lower straight portions 71*b* (L) and 72*b* (L) of the plastic plate 30B on the reverse side are curved in predetermined directions. The distal ends of the upper straight portions 71*a* (U) and 72*a* (U) of the plastic plate 30B on the reverse side are not curved, and are shorter than the upper straight portions 71*a* (U) and 72*a* (U) of the plastic plate 30A on the obverse side. Distal end faces A of the upper straight portions 71*a* (U) and 72*a* (U) of the plastic plate 30B on the reverse side form tilted surfaces that are tilted at the same angle (45°) as the tilt angle of a nip portion 10B of the trial lens 10.

Of the surface of the plastic plate 30A on the obverse side, the downward-curved distal end of each of the upper straight portions 71*a* (U) and 72*a* (U) has figures "28", "30", "32", "34", and "36" (30, 32, and 34 are not shown) respectively expressing the PD values from the center of the lens holding frame 70, and five equidistant scale marks 76 indicating the positions of these figures. The scale marks 76 on the rim 71, which is on the left side when seen by the person to be tested, are tilted to the left by 45°, and those on the right rim 72 are tilted to the right by 45°. The scale marks indicating "28" overlap the distal end faces A of the upper straight portions 71*a* (U) and 72*a* (U), respectively, of the plastic plate 30B on the reverse side. When the scale marks 76 are formed on the distal ends of the surfaces of the straight portions 71*a* (U) and 72*a* (U) of the plastic plate 30A on the obverse side to be tilted by 45° in this manner, the PD can be adjusted by means of the positions of the nip portions 10B of the trial lenses 10. For example, assume that the PD value of the person to be tested is 56. When the PD of a left-eye trial lens 10L is to be adjusted, the left-eye trial lens 10L is inserted in the accommodating space 8A of the left rim 71, and the nip portion 10B is abutted against the distal end face A of the left straight portion 71*a* (U) of the plastic plate 30B on the reverse side so as to coincide with the scale mark 76 indicating the value "28". Similarly, when the PD of a right-eye trial lens 10R is to be adjusted, the right-eye trial lens 10R is inserted in the accommodating space 8B of the right rim 72, and the nip portion 10B is abutted against the distal end face A of the straight portion 72*a* (U) of the plastic plate 30B on the reverse side so as to coincide with the scale mark 76 indicating the value "28". Consequently, the PD values of the left and right trial lenses 10 are adjusted to 56 mm. When adjusting the PD value to 60 mm, the trial lens 10 may be moved outwardly, such that that upper tilted surfaces 77 of the nip portions 10B coincide with the scale marks 76 indicating the value "30".

Four vertical lines 78*a* to 78*d* and two horizontal lines 79*a* and 79*b* are formed on the outer surface of the connecting portion 73. The four vertical lines 78*a* to 78*d* facilitate center alignment with the existing glass frame. The two inner vertical lines 78*a* and 78*b* are for a small frame, while the two outer vertical lines 78*c* and 78*d* are for a large frame. Of the two horizontal lines 79*a* and 79*b*, the lower horizontal line 79*a* is a datum line (geometric horizontal line) running through the centers of the left and right rims 71 and 72. The upper horizontal line 79*b* indicates the height of the eye point of the progressive diopter lens, and is located above the datum line 79*a* by 4 mm. The positions of the eye points are where the glances pass in the state of an ordinary field of view when the test tool for optometry is mounted on the glasses at the reference position of fitting (usually slightly below the positions of pupils).

Two triangular marks 80 each indicating the center in the right-to-left direction of the lens holding frame 70 are formed at the center of the surface of the connecting portion 73 to vertically oppose each other. When mounting the lens holding frame 70 on the glasses, if the marks 80 are set to coincide with the center of the bridge of the glasses, the shift in the left-to-right direction is adjusted. A recess 20 where a finger is to be inserted, and a nose relief recess 21 are formed above and under the connecting portion 73.

Figure 10:
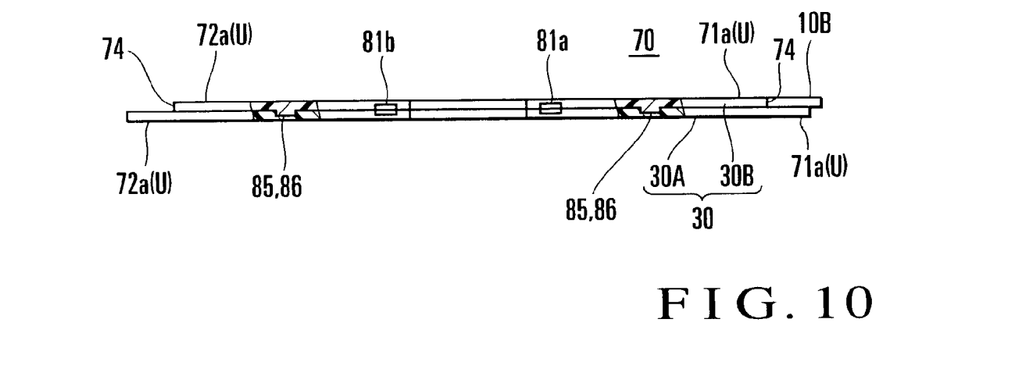
FIG. 10 is a plan view of the lens holding frame.
Figure 11:
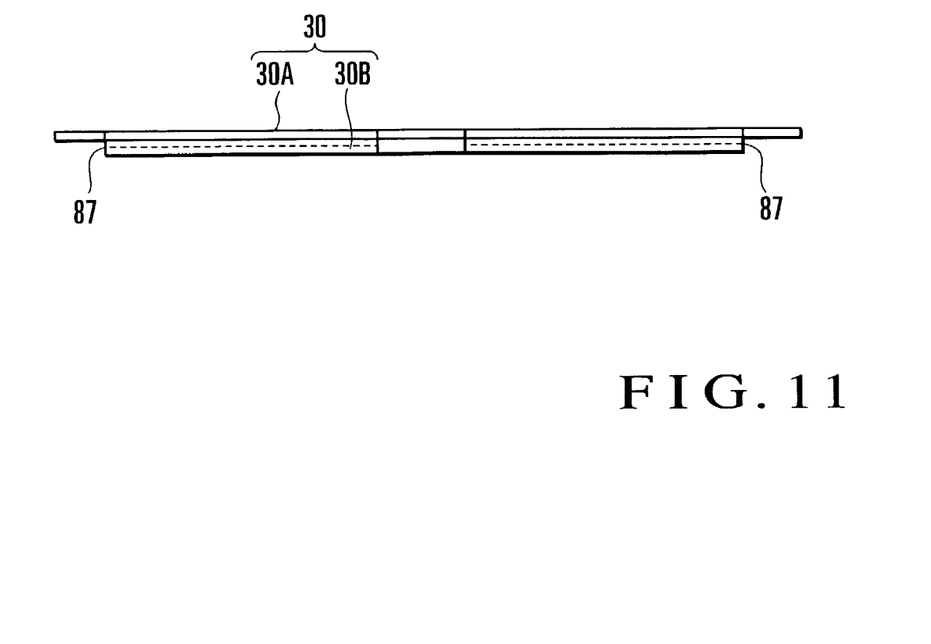
FIG. 11 is a bottom view of the lens holding frame.

In the upper surface of the lens holding frame 70, vertically elongated rectangular holes 81*a* and 81*b*, where legs 36*a* and 36*b* of a support arm 36 identical to that shown in FIG. 1 are to be inserted, are formed between the bonding surfaces of the two plastic plates 30A and 30B. Two screw attaching holes 83 for the holes 81*a* and two screw attaching holes 83 for the holes 81*b* are formed in the plastic plate 30B on the reverse side, resulting in a total of four screw attaching holes 83. The legs 36*a* and 36*b* are fixed in the holes 81*a* and 81*b* with machine screws 35 (see FIG. 1) screwed in the screw attaching holes 83.

Figure 12:
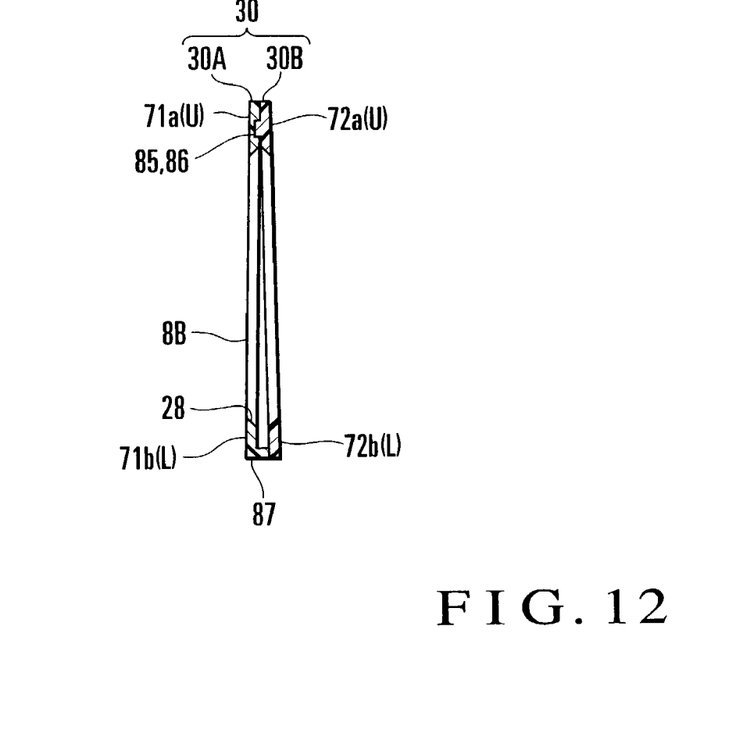
FIG. 12 is a sectional view taken along the line XII—XII in FIG. 9.

The two plastic plates 30A and 30B are positioned by fitting recesses 85 and positioning projections 86 formed in the bonding surfaces of the upper straight portions 71*a* (U) and 72*a* (U) of the rims 71 and 72, respectively. Thus, the upper straight portions 71*a* (U) and 72*a* (U) of the rims 71 and 72 are brought into tight contact with each other, and are integrally connected to each other by the four machine screws 35 that are screwed in the respective screw attaching holes 83 in order to fix the legs 36*a* and 36*b* of the support arm 36. Lower straight portions 71*a* (L) and 72*b* (L) of the two plastic plates 30A and 30B are brought into tight contact with each other through a spacer 87 projecting from the lower surface of the plastic plate 30A on the obverse side, and are integrally bonded to each other with an adhesive.

In the lens holding frame 70 with the above structure, the upper tilted surface 77 of the nip portion 10B of each trial lens 10 need only be set to coincide with the scale mark 76 indicating the PD value from the center of the lens holding frame 70 in accordance with the PD of the person to be tested. Thus, the PD adjusting operation is easy, and can be performed reliably. In other words, the PD value can be confirmed by visually checking which one of the five scale marks 76 the upper tilted surface 77 of the nip portion 10B coincides with. Due to the presence of the horizontal line 79*b* for the eye point, the height position of the eye point can be obtained.

In the embodiments described above, the lens holding frame 3 or 70 is formed by adhering the two plastic plates 30. However, the present invention is not limited to this, and the lens holding frame 3 or 70 may be formed of one injection-molded plastic plate. In this case, the rims are C-shaped, the open end widths W of the rims are smaller than the widths of the interiors of the rims, and the V-shaped lens holding grooves 28 are formed in the inner surfaces of the rims. Thus, forced mold release is required. If the rims are elastically deformable, the lens holding frame can be formed by injection molding. Alternatively, the lens holding frame may be fabricated by machining one injection-molded plastic plate.

As has been described above, the test tool for optometry according to the present invention is formed of a lens holding frame and a clip. The lens holding frame is formed of a pair of axi-symmetrical C-shaped (or sideway-inverted U-shaped) rims and a connecting portion. Each rim has an open end and closed end. The closed ends oppose each other.

The connecting portion connects the closed ends of the rims. The inner spaces of the respective rims form trial lens accommodating spaces. Lens holding grooves for holding the trial lenses to be pivotal and movable in the left-to-right direction are formed in the inner surfaces of the rims, respectively. Thus, the structure is simple and the number of components is small, thus realizing weight reduction and cost reduction. The eyesight can be tested by utilizing the existing glasses. The test tool for optometry can be mounted on and removed from the glasses easily, and the trial lenses can be inserted in and removed from the lens holding grooves simply and easily. Thus, a test tool for optometry that can be handled easily can be provided. Since this test tool for optometry imposes small physical burden to the person to be tested, it is suitably used particularly when he is to experience how he can see a far portion and near portion with progressive multifocal trial lenses on.

If the lens holding frame is formed of two plastic plates having substantially the same shape, it can be fabricated at a low cost. The fabricating cost is also low when the lens holding frame is formed of one plastic plate.

If projections that narrow the open end widths of the rims are formed, they can reliably prevent trial lenses from dropping from the lens holding grooves. If the trial lenses ride over the projections, the rims of the lens holding frame elastically deform to widen the open end widths. Thus, the trial lenses can be removed from the lens holding grooves easily.

What is claimed is:

1. A test tool for optometry comprising:
   a lens holding frame for pivotally supporting a trial lens to be mounted, and a clip attached to a rear side of said lens holding frame to clamp glasses, wherein
   said lens holding frame comprises a pair of axi-symmetrical C-shaped rims having open ends and opposing closed ends, and a connecting portion that connects at least a central portion of each of the opposing closed ends of the rims, and
   each of said rims has an inner surface that forms an accommodating space for holding the trial lens to be pivotal and movable in a left-to-right direction.

2. A tool according to claim 1, wherein said lens holding frame is integrally formed by placing one upon another and bonding two plastic plates having substantially the same shape.

3. A tool according to claim 2, wherein a lens holding groove is formed in the inner surface of each of said rims.

4. A tool according to claim 1, wherein said lens holding frame integrally has projections for narrowing open end widths of said rims, respectively.

5. A tool according to claim 1, wherein a width of the open ends of each of said rims is set smaller than an outer diameter of the trial lens so that the trial lens to be mounted does not drop.

6. A tool according to claim 1, wherein said lens holding frame further comprises holding means for holding the trial lens at a position of a half-value of PD from a center of said lens holding frame when the trial lens is mounted on said lens holding frame.

7. A tool according to claim 6, wherein the trial lens to be mounted has a lens portion and a nip portion, and
   said holding means is a stopper for holding said nip portion of the trial lens to be mounted at a predetermined angle.

8. A tool according to claim 1, wherein said lens holding frame has a sign at a position corresponding to a half-value of a PD from a center of said lens holding frame when the trial lens is mounted therein.

9. A tool according to claim 1, wherein the accommodating space for the trial lens which is formed on the inner surface of each of said rims holds the
   trial lens to be pivotal and movable in the left-to-right direction, and has such a shape that the trial lens is held at a position corresponding to a half-value of a PD from a center of said lens holding frame.

10. A tool according to claim 1, wherein said lens holding frame has a horizontal line for an eye point.

11. A tool according to claim 1, wherein said lens holding frame has a nose relief recess under said connecting portion.

* * * * *